United States Patent [19]

Kabara

[11] 3,934,035
[45] Jan. 20, 1976

[54] CERTAIN AMINIMIDES USED TO CONTROL BACTERIA AND FUNGI

[75] Inventor: Jon J. Kabara, Okemos, Mich.

[73] Assignee: Michigan State University, East Lansing, Mich.

[22] Filed: Apr. 29, 1974

[21] Appl. No.: 465,121

[52] U.S. Cl. ................................................. 424/320
[51] Int. Cl.² ............................................ A01N 9/20
[58] Field of Search ..................................... 424/320

[56] References Cited
UNITED STATES PATENTS 3,409,646  11/1968  Sims et al. ................... 424/320 X
3,485,806  12/1969  Bloomquist et al. ......... 260/348 C X Primary Examiner—Leonard Schenkman

[57] ABSTRACT

A class of aminimides structurally characterizable as dipolar ions wherein a quaternary nitrogen atom is directly bonded to the nitrogen anion of methyacrylamide exhibit broad spectrum inhibitory activity against gram positive bacteria and fungi.

8 Claims, No Drawings

CERTAIN AMINIMIDES USED TO CONTROL BACTERIA AND FUNGI

BACKGROUND OF THE INVENTION

1. Field of the Invention

This invention relates to a class of nitrogenous compounds as antimicrobial agents for the control of bacterial and fungal growth.

2. Description of the Prior Art

Considerable effort has been directed during the past several decades towards developing antimicrobial agents having a high activity against a broad spectrum of microorganisms including bacteria and fungi, but which at the same time exhibit acceptably tolerable physiological properties. It is generally accepted that hexachlorophene of all of such antimicrobials proposed to date comes about the closest to meeting these desiderata. Unfortunately the use of halogenated compounds of this type has been severely restricted because of the recent unfortunate events stemming from what many feel amounted to a conspicuous misuse of hexachlorophene. Accordingly a present need exists for an effective antimicrobial of this type devoid of the chemical characteristics associated with the indicated halogenated compounds.

It has recently been reported that certain fatty amines and fatty amides evidence antimicrobial activity. Although the activity of these compounds fails to measure up to that demanded for a practical antimicrobial agent, the low order of toxicity attributed to compounds of this type renders these findings highly significant.

SUMMARY OF THE INVENTION

In accordance with the present invention a method is provided for inhibiting the growth of bacteria and fungi which comprises applying to said organisms or their loci an antimicrobially effective amount of a compound of the formula

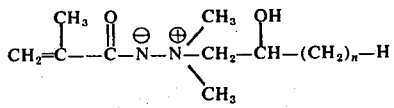

wherein n is an integer of from 1–16.

The antimicrobial agents of this invention in essentially micro concentrations exhibit surprisingly effective broad spectrum inhibitory activity against gram positive and fungal organisms. Moreover, the dipolar ion characteristics of these compounds contribute towards their marked hydrophilic nature and neutrality, which properties are important in numerous use applications especially where detergency constitutes an adjunct function.

DESCRIPTION OF THE PREFERRED EMBODIMENTS

As indicated previously the practice of this invention resides in the use of the antimicrobial agents described above as the active ingredient in a variety of conventional compositions for medicinal, cosmetic or disinfectant purposes. These compositions can be in the form of solutions, as well as solid, liquid or pasty suspensions and emulsions wherein the carrier or vehicle portion is water, oil, or an organic solvent, such as, for example, ethanol. Likewise these compositions can be solid admixtures including the pulverulent form thereof Representative of the foregoing compositions include cosmetic oils, salves, creams, pencils and powders; personal care items such as the spray, stick or powder deodorants, mouthwashes, hair rinses, skin lotions, foot powders and the like; and cleaning compositions such as detergent bars, shampoos and toothpastes. Further, the antimicrobial agents of this invention can be advantageously employed in washing, rinsing, cleaning, disinfecting and preserving compositions for textiles, leather, etc. Still a further important use of these agents can be found in the cleaning and disinfecting compositions designed for use in hospitals and such cleanlinss sensitive industrial establishing as dairies, breweries and laundries. The amount of the antimicrobial agent present in the contemplated compositions obviously depends on the particular use for which the overall composition is designed. Generally, in toothpaste, deodorants, cosmetics and foot powders and the like the amount of the antimicrobial agent ranges from about 0.1 to 3.0% based on the total weight of the composition. In applications of a cleansing and disinfecting nature as noted above, the concentration of the agent in these instances can range up to about 10.0%.

The antimicrobial compounds contemplated herein can readily be prepared by reacting approximately stoichiometrical proportions of a methacrylate, preferably a lower alkyl ester thereof, 1-1-dimethyl hydrazine and a 1,2-olefin oxide. Examples of the olefin oxides utilized in preparing the various text compounds shown hereinbelow include propylene oxide, α-octyl oxide, α-decyl oxide, α-dodecyl oxide and α-hexadecyl oxide. The reaction can be effected simply by heating the indicated reactants at a temperature preferably between 20° C. and 80° C. and recovering the product by the usual crystallization procedures. Complete details relative to the above-described method for deriving the contemplated aminimides can be found in U.S. Pat. 3,485,806.

EXAMPLE

For the purpose of illustrating the antimicrobic activity of the aminimides of the present invention, five gram positive bacteria and two representative fungi were used in a conventional test procedure for determining inhibitory effect. The identification of these test organisms and their source follows:

| Organism | Source |
| --- | --- |
| Streptococcus faecalis (grp. D) | Clinical Isolate |
| Streptococcus pyogenes | " |
| Staphylococcus aureus | Hospital Infection |
| Corynebacterium | ATCC No. 10700 |
| Nocardia asteroides | ATCC No. 3308 |
| Saccaharomyces cerevisiae | Fleishman |
| Candida albicans | Michigan State University |

In the test procedures observed, representative aminimides were dissolved in water or 95% ethanol to provide standard solutions having a concentration of 1.0 mg of the test compound per ml of the solvent. A further test series was prepared by diluting with sterile Trypticase Soy Broth to concentrations of 100 ug/ml. Compounds more active than at 100 ug/ml were further diluted in a subsequent test.

Following the preparation of the test solutions as noted above, one drop (0.04 ± 0.01 ml.) of an 18-hour broth culture containing $10^9$ to $10^{12}$ organisms per ml. was added to about 10 cc of each starting dilution of the indicated test compounds as well as to a like sample of plain broth serving as a positive control. After innoculation, the test samples are thoroughly mixed and then incubated at 35°C. in a 5% carbon dioxide atmosphere.

After an 18 hour period of incubation, the minimal inhibitory concentration (MIC) of each compound was determined for each test microorganism. The MIC value is defined as the lowest concentration (ug/ml) of the test compound at which no microscopic evidence of growth is observed. In those instances where the MIC exceeded 1000 ug/ml the compound was rated non-inhibitory (NI). Under those circumstances where the test compound itself causes turbidity so that the MIC proved difficult to determine in accordance with the above procedure, a sample (0.015 ml.) of the well-agitated broth or broths in question were innoculated into a Trypticase Soy agar plate containing 5% defibrinated sheep blood. The test plate would then be incubated at 35° C. for 18 hours and thereupon examined for growth.

The identification of representative compounds tested in accordance with the foregoing procedure together with the results obtained are outlined in the following Table I.

What is claimed is:

1. A method of inhibiting the growth of bacteria and fungi which comprises applying to said organisms or their loci an antimicrobially effective amount of a compound of the formula

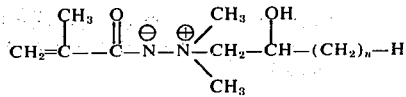

wherein n is an integer of from 1–16.

2. The method of claim 1 wherein n of said formula is 1.
3. The method of claim 1 wherein n of said formula is 6.
4. The method of claim 1 wherein n of said formula is 8.
5. The method of claim 1 wherein n of said formula is 10.
6. The method of claim 1 wherein n of said formula is 12.
7. The method of claim 1 wherein n of said formula is 14.
8. The method of claim 1 wherein n of said formula is 16.

TABLE I $$CH_2=C(CH_3)-C(O)-N^{\ominus}-N^{\oplus}(CH_3)-CH_2-CH(OH)-(CH_2)_n-H$$

| COMPOUND - n = | 1 | 6 | 8 | 10 | 12 |
|---|---|---|---|---|---|
| *Streptococcus faecalis* (grp. D) | 1000 | NI | 1000 | 100 | 10 |
| *Streptococcus pyogenes* | 1 | 1000 | 10 | 10 | 10 |
| *Staphylococcus aureus* | 100 | 1000 | 1000 | 100 | 10 |
| *Cornyebacterium* | 100 | 1000 | 1000 | 100 | 10 |
| *Nocardia asteroides* | 1000 | 1000 | 100 | 100 | 10 |
| *Candida albicans* | 1000 | NI | 1000 | 100 | 100 |
| *Saccharomyces cerevisiae* | 10 | NI | 1000 | 100 | 1 |